United States Patent
Tao et al.

(10) Patent No.: US 6,476,007 B2
(45) Date of Patent: Nov. 5, 2002

(54) ISOFORM SPECIFIC INHIBITION FOR TREATMENT OF PAIN AND REDUCTION OF ANESTHETIC THRESHOLD

(75) Inventors: Yuanxiang Tao, Baltimore; Roger A. Johns, Reistertown, both of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/731,876

(22) Filed: Dec. 8, 2000

(65) Prior Publication Data

US 2001/0031750 A1 Oct. 18, 2001

Related U.S. Application Data

(60) Provisional application No. 60/170,260, filed on Dec. 8, 1999.

(51) Int. Cl.$^7$ .............................................. A61K 31/675
(52) U.S. Cl. ...................................................... 514/81
(58) Field of Search ........................................... 514/81

(56) References Cited

U.S. PATENT DOCUMENTS 5,625,056 A    4/1997   Genieser et al.

OTHER PUBLICATIONS

E. Butt et al., "(Rp)–8–pCPT–cGMPS, a Novel cGMP–Dependent Protein Kinase Inhibitor", European Jour. Of Pharmacology, No. 269, 1994, pp. 265–268.

Y. Tao et al., "Activation of cGMP–Dependent Protein Kinase Iα Is Required For N–Methyl–D–Aspartate–Or Nitric Oxide–Produced Spinal Thermal", European Jour. Of Pharmacology, No. 392, 2000, pp. 141–145.

Y. Tao et al., "Expression And Action Of Cyclic GMP–Dependent Protein Kinase Iα In Inflammatory Hyperalgesia In Rat Spinal Cord", Neuroscience, vol. 95, No. 2, 2000, pp. 525–533.

Butt, Elke, et al., (Rp)–8–pCPT–cGMPS, a novel cGMP–dependent protein kinase inhibitor, European Journal of Pharmacology Molecular Pharmacology Section 269, 1994, pp. 265–268, vol. 17, No. 2, Elsevier Science.

Lewin, Matthew R., et al., "Cyclic GMP pathway is critical for inducing long–term sensitization of nociceptive sensory neurons," Nature *Neuroscience*, Jan. 1999, pp. 18–23, vol. 2, No. 1.

Sluka, K.A., et al., "The effects of G–protein and protein kinase inhibitors on the behavioural response of rats to intradermal injection of capsaicin," Internal Association for the Study of Pain, pp. 165–178, vol. 71, No. 2, Elsevier Science, 1997.

Tao, Yuan–Xiang, et al., "Involvement of cGMP–Dependent Protein Kinase I Alpha in the Spinal Hyperalgesia," Nitric Oxide, Jun. 3–7, 2000, vol. 4, No. 3, Abstract from First International Conference on Biology Chemistry, and Therapeutic Application of Nitric Oxide, San Francisco, CA.

*Primary Examiner*—William R. A. Jarvis
(74) *Attorney, Agent, or Firm*—Banner & Witcoff, Ltd.

(57) ABSTRACT

Several lines of evidence have shown a role for the nitric oxide (NO)/cyclic guanosine monophosphate (cGMP) signaling pathway in the development of spinal hyperalgesia. However, the roles of effectors for cGMP are not fully understood in the processing of pain in the spinal cord. cGMP-dependent protein kinase (PKG) Iα but not PKGIβ was localized in the neuronal bodies and processes, and was distributed primarily in the superficial laminae of the spinal cord. Intrathecal administration of an inhibitor of PKGIα, Rp-8-[(4-Chlorophenyl)thio]-cGMPS triethylamine, produces significant antinociception. Moreover, PKGIα protein expression was dramatically increased in the lumbar spinal cord after noxious stimulation. This upregulation of PKGIα expression was completely blocked not only by a neuronal NO synthase inhibitor, and a soluble guanylate cyclase inhibitor, but also by an N-methyl-D-aspartate (NMDA) receptor antagonist, MK-801. Noxious stimulation not only initially activates but also later upregulates PKGIα expression in the superficial laminae via an NMDA-NO-cGMP signaling pathway, suggesting that PKGIα plays an important role in the central mechanism of inflammatory hyperalgesia in the spinal cord.

24 Claims, 11 Drawing Sheets

FIG. 5

Table 1. Effect of intrathecally administered Rp-8-pCPT-cGMPS (10, 20 and 30 μg) on formalin-induced nociception in the rat

|        | Vehicle        | 10 μg          | 20 μg            | 30 μg            |
|--------|----------------|----------------|------------------|------------------|
| Phasic | 53.25 ± 7.25   | 54.75 ± 6.21   | 45.50 ± 4.14     | 19.5 ± 3.65**    |
| Tonic  | 503.25 ± 16.75 | 537.50 ± 32.20 | 378.75 ± 23.42** | 172.00 ± 16.25** |

Number of flinches and shakes in the phasic and tonic periods of the formalin test was counted as described under Experimental Procedures. Each value is the mean ± S.E.M.

**$P < 0.01$ for Rp-8-p-CPT-cGMPS-treated groups vs vehicle-treated control groups.

FIG. 7

Table 2. Effect of intrathecally administered Rp-8-pCPT-cGMPS (10, 20 and 30 μg) on formalin-induced *c-fos* expression in the rat

|  | Vehicle | 10 μg | 20 μg | 30 μg |
| --- | --- | --- | --- | --- |
| Laminae I–II | 26.72 ± 0.77 | 23.44 ± 1.30 | 22.60 ± 0.98* | 18.90 ± 1.47** |
| Laminae III–IV | 7.92 ± 0.50 | 7.52 ± 0.68 | 7.60 ± 0.67 | 5.58 ± 0.55* |
| Laminae V–VI | 23.00 ± 1.44 | 20.26 ± 1.43 | 14.88 ± 1.14** | 11.38 ± 0.56** |
| Laminae VII–X | 6.72 ± 1.64 | 7.54 ± 0.57 | 7.78 ± 0.54 | 6.71 ± 0.30 |

Number of Fos-positive neurons in the spinal cord was counted as described under Experimental Procedures. Each value is the mean ± S.E.M.
*$P < 0.05$, **$P < 0.01$ for Rp-8-p-CPT-cGMPS-treated groups vs vehicle-treated control group.

FIG. 8B

Table 3. Quantitative changes in cyclic guanosine monophosphate-dependent protein kinase I$\alpha$ in lumbar enlargement segments of the spinal cord from animals (0 h) and treated animals 24, 48 and 96 h after saline or formalin injection

|          | 0 h (control) | 24 h          | 48 h          | 96 h           |
|----------|---------------|---------------|---------------|----------------|
| Saline   | 1             | 0.95 ± 0.16   | 1.24 ± 0.15   | 1.10 ± 0.18    |
| Formalin | 1             | 1.19 ± 0.14   | 1.34 ± 0.10   | 1.70 ± 0.13*#  |

US 6,476,007 B2

ISOFORM SPECIFIC INHIBITION FOR TREATMENT OF PAIN AND REDUCTION OF ANESTHETIC THRESHOLD

This application claims the benefit of provisional application No. 60/170,260, filed Dec. 8, 1999, which is expressly incorporated by reference in its entirety herein.

TECHNICAL FIELD OF THE INVENTION

The U.S. government retains certain rights in the invention according to the provisions and conditions of NIH grants RO1 GM 49111.

BACKGROUND OF THE INVENTION

Nitric oxide (NO), which serves as an intracellular messenger, is implicated in a number of processes in the central nervous system. In the spinal cord, considerable evidence has demonstrated that NO contributes to the development of hyperalgesia in models of acute and chronic pain (Meller and Gebhart, 1993). Noxious stimulation increased NO synthase (NOS) expression (Lam et al., 1996) and cyclic guanosine 3', 5-monophosphate (cGMP) content (Garry et al., 1994b) in the spinal cord. Administration of inhibitors of NOS and soluble guanylate cyclase caused analgesic effects (Malmberg and Yaksh, 1993; Meller et al., 1992a, b; Moore et al., 1990). Moreover, NO donors and cGMP analogues applied intrathecally caused a reduction in tail flick or paw withdrawal latency (Garry et al., 1994a; Inoue et al., 1997). Recently, sodium nitroprusside (an NO donor) was shown to evoke the release of immunoreactive cGMP from dorsal horn slices, which was suppressed by the application of methylene blue (a soluble guanylate cyclase inhibitor) (Garry et al., 1994c). These data indicate that the NO/cGMP signaling pathway contributes to spinal hyperalgesia via a cGMP-dependent mechanism.

It has been demonstrated that the N-methyl-D-aspartate (NMDA) receptors play a key role in multisynaptic nociceptive transmission and plasticity within the spinal cord (Aanonsen et al., 1990; Dickenson and Aydar, 1991). The NMDA receptors may be involved in changes such as central sensitization, wind-up, facilitation, hyperalgesia and allodynia, all of which may be manifestations of the same mechanisms. It is found that many of the effects of NMDA receptor activation appear to be ultimately mediated through the production of NO and cGMP (Meller and Gebhart, 1993). In the cerebellum, NMDA receptor activation results in a $Ca^{2+}$-dependent increase in cGMP through the production of NO (Garthwaite et al., 1988). In the spinal cord, NMDA-produced facilitation of the tail flick reflex was completely abolished by pretreatment with either an NOS inhibitor ($N^G$-nitro-L-arginine methyl ester) or a soluble guanylate cyclase inhibitor (methylene blue) (Meller et al., 1992a). Moreover, NMDA has been demonstrated to directly produce the release of NO in vivo at the spinal cord level (Rivot et al., 1999). These results indicate that NMDA may produce thermal hyperalgesia through the activation of the NO/cGMP signaling system in the spinal cord.

The NO/cGMP signaling pathway modifies several intracellular processes including activation of protein kinase, ion channels and phosphodiesterases. cGMP-dependent protein kinases are serine/threonine protein kinases and belong to the large family of protein kinases. cGMP-dependent protein kinases have been found to serve as major effectors for the NO/cGMP signaling pathway in the vascular and nervous system (Meller and Gebhart, 1993). Two isoenzymes of cGMP-dependent protein kinase have been recognized in mammals: cytosolic cGMP-dependent protein kinase I and membrane-bound cGMP-dependent protein kinase II. Furthermore, cGMP-dependent protein kinase I has been shown to exist in two isoforms, designated Iα and Iβ.

Sluka and Willis (1997) reported that the mechanical allodynia induced by capsaicin could be reversed by KT5823, a selective cGMP-dependent protein kinase but not selective cGMP-dependent protein kinase isoform inhibitor. There is a need in the art for drugs which will treat pain without having undesirable side effects.

The nitric oxide/cyclic guanosine monophosphate (NO/cGMP) signaling pathway has become increasingly important as our understanding of its diverse biological actions has expanded, especially within the central nervous system (1, 2). The best understood trigger for the NO/cGMP signaling pathway in the central nervous system is the opening of N-methyl-D-aspartate (NMDA) receptor channels and the activation of NO synthase (NOS) in a $Ca^{2+}$-dependent manner. NO then results in cGMP formation in adjacent neurons through the activation of soluble guanylate cyclase (sGC) (3, 4). Considerable evidence has demonstrated that the NO/cGMP signaling pathway is present in the neurons of the spinal cord and contributes to the development of hyperalgesia in models of acute and chronic pain (4, 5).

SUMMARY OF THE INVENTION

It is an object of the invention to provide a method of affecting nociception.

It is an object of the invention to provide a catheter for treating pain.

It is an object of the invention to provide a pharmaceutical composition for treating pain.

It is an object of the invention to provide a method for screening for drugs useful in the treatment of pain.

These and other objects of the invention are provided by one or more of the embodiments described below. In one embodiment of the invention a method of affecting nociception is provided. An analgesic amount of an inhibitor of cyclic guanosine monophosphate (cGMP)-dependent protein kinase Iα (PKGIα) is administered to a patient in need thereof. Desirably, the inhibitor preferentially inhibits isoenzyme I relative to isoenzyme II and inhibits isoform Iα relative to isoform Iβ.

According to another embodiment of the invention another method of affecting nociception is provided. An analgesic amount of Rp-8-[(4-Chlorophenyl)thio]-cGMPS triethylamine (Rp-8-CPT-cGMPS) or other inhibitor of cyclic guanosine monophosphate (cGMP)-dependent protein kinase Iα (PKGIα) is administered intrathecally to a patient in need thereof.

Another aspect of the invention is a catheter. The catheter comprises an analgesic amount of an inhibitor of cyclic guanosine monophosphate (cGMP)dependent protein kinase Iα (PKGIα). Desirably, the inhibitor preferentially inhibits isoenzyme I relative to isoenzyme II and preferentially inhibits isoform α relative to isoform β.

According to another embodiment of the invention a pharmaceutical composition for treating pain is provided. The composition comprises Rp-8-CPT-cGMPS or another inhibitor of cyclic guanosine monophosphate (cGMP)-dependent protein kinase Iα (PKGIα) in a sterile, pyrogen-free, aqueous vehicle.

In yet another aspect of the invention a method of screening for drugs useful in the treatment of pain is provided. A compound is tested for the ability to inhibit PKG Iα. The compound is also tested for the ability to inhibit PKG Iβ. A compound is identified as a candidate drug useful in the treatment of pain if it selectively inhibits PKG Iα relative to PKG Iβ.

Another embodiment of the invention is another method for screening for drugs useful in the treatment of pain. Cells are contacted with a test compound. Transcription, activity, or translation of PKG Iα is monitored in the cells. A compound is identified as a candidate drug if it inhibits transcription, activity, or translation of PKG Iα.

The present invention thus provides the art with new targets, new drugs, and new methods for treating pain.

BRIEF DESCRIPTION OF THE DRAWINGS

FIG. 5 Effect of intrathecally administered Rp-8-p-CPT-cGMPS (10, 20 and 30 μg) on formalin-induced nociception in the rat. The number of flinches and shakes produced by formalin was counted as described under Methods. **$p<0.01$ for Rp-8-p-CPT-cGMPS-treated groups vs water-treated control groups.

(FIG. 6A) In intrathecally water-treated animals, numerous Fos-positive neurons were observed in the dorsal horn, particularly in laminae I, II, V and VI. (FIG. 6B) In intrathecally Rp-8-p-CPTc-GMPS (30 μg)-treated animals, the number of Fos-positive neurons was significantly decreased in the dorsal horn compared to (FIG. 6A). Scale bar: 200 μm.

FIG. 7 Effect of intrathecally administered Rp-8-p-CPT-cGMPS (10, 20 and 30 μg) on formalin-induced c-fos expression in the rat. Number of Fos-positive neurons in laminae I–II, III–IV and V–VI was significantly decreased (*$p<0.05$, **$p<0.01$) after intrathecal administration of Rp-8-p-CPT-cGMPS (20 μg and 30 μg) when compared to tissues from water pretreated rats. A low dose of Rp-8-p-CPT-cGMPS (10 μg) was ineffective. There was no signifi-cant reduction of the number of Fos-positive neurons in laminae VII–X treated with Rp-8-p-CPT-cGMPS and water.

FIG. 8A and FIG. 8B. Expression and quantitative changes of PKGIα in the lumbar enlargement segments of the spinal cord from control animals (0 hour) and treated animals 24, 48 and 96 hours after saline or formalin injection. The upper panel (FIG. 8A) depicts a representative western blot, in which the normal lung (L) was used as a positive control for PKGIα. The lower panel (FIG. 8B) is the statistical summary of the densitometric analysis expressed relative to normal control groups. *$p<0.05$ for formalin-treated groups vs corresponding saline-treated groups. #$p<0.05$ for formalin-treated groups vs corresponding normal control groups FIGS. 9(A and B) Distribution of PKGIα immunoreactivity in the fifth lumbar segment of the spinal cord from treated animals 96 hours after formalin injection (FIG. 9A, FIG. 9B).

DETAILED DESCRIPTION OF THE INVENTION

Figure 1:
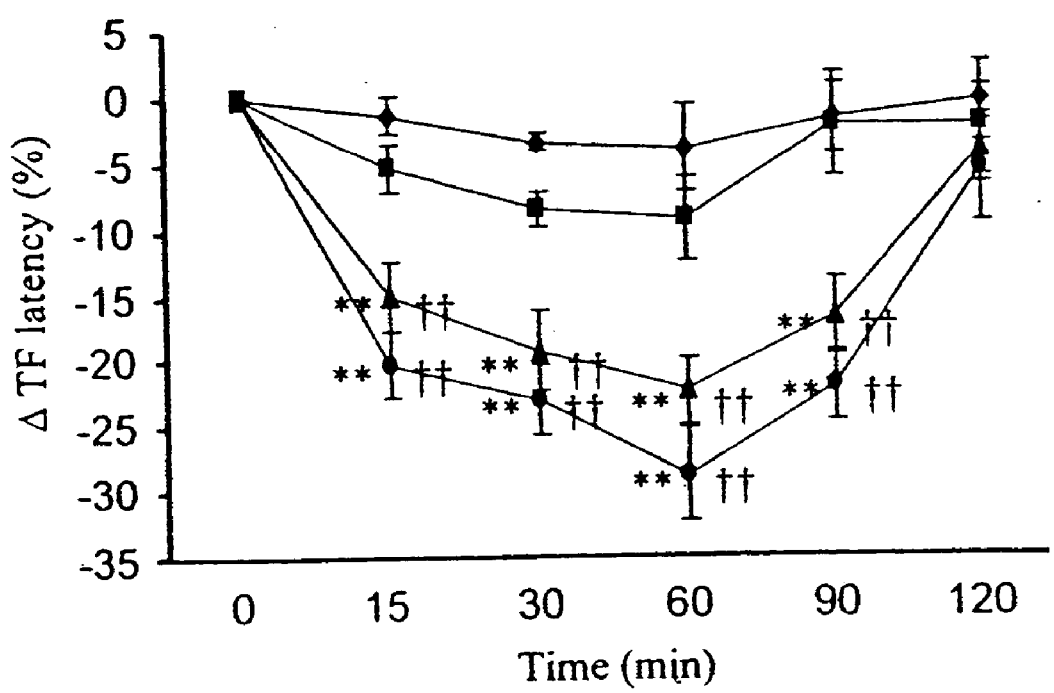
FIG. 1. Time course of the effects of intrathecally injected NOC-12 on the tail-flick latency in rats. Saline control (♦); 10 μg of NOC-12 (■); 20 μg of NOC-12 (▼); 30 μg of NOC-12 (●). All agents were dissolved in 0.9% saline before 1injection. Intrathecal NOC-12 produced curtailment of the tail-flick latency in a dose-dependent manner. Data represent the mean±S.E.M. **$p<0.01$ vs saline-treated groups. ††$p<0.01$ compared with pre-examination (0 min) value in the same group.

It is a discovery of the present inventors that activation of cGMP-dependent protein kinase Iα is required for NMDA or nitric oxide produced hyperalgesia. It is a further discovery of the inventors that such hyperalgesia can be treated using inhibitors of PKG Iα. Any such inhibitor can be used, however preferred properties include relative non-inhibition of the PKG Iβ isoform, and the PKG II isoenzyme. In addition the inhibitor should not affect either cAMP-dependent protein kinases or cGMP phosphodiesterases. A particularly suitable compound according to the invention is Rp-8-p-CPT-CGMPS. (Also known as Rp-8-[(4-Chlorophenyl)thio]-guanosine 3',5'-cyclic monophosphothioate triethylamine; Rp-8-p-CPT-cGMPS Rp-8-[(4-Chlorophenyl)thio]-guanosine-cyclic 3',5'-hydrogen phosphorothioate.) It has the additional desirable properties of solubility in water or saline, no observed side-effects, and no effect on the cardiovascular system. Other inhibitors can be identified as described here. Attractive candidates for testing are other analogues of cGMP. Particularly attractive candidates are those which interact with the active site of PKG Iα. Such inhibitors are useful clinically to decrease the need for anesthetics, particularly inhalational anesthetics and to reduce acute and chronic pain.

Applicants do not wish to be bound by any particular theory regarding mechanism of action. However, the data collected suggest the following model for nociceptive reflexes produced by NMDA in the spinal cord: NMDA receptor activation increases intracellular $Ca^{2+}$ content which activates the calmodulin site on neuronal NOS to produce NO from the amino acid precursor, L-arginine. NO then activates soluble guanylate cyclase to increase intracellular content of cGMP, which results in the activation of cGMP-dependent protein kinase Iα within the target cells.

Nociception is the ability to feel pain. Any noxious stimulation of the neuronal system, especially of the spinal cord is contemplated for treatment within the scope of the invention. The pain can be acute or chronic, involving inflammation or mechanical impinging on a nerve.

Administrations of analgesics and inhibitors according to the invention can be by any means known in the art, so long as the agents are able to reach their targets. Thus agents can be administered without limitation intravenously, intracerebrally, intrathecally, transdermally, intraarterially, topically, isubcutaneously, intradermally, orally, nasally, by inhalation, or intramuscularly. Administration may be given once, repeatedly, or chronically. For intrathecal administration a special catheter can be used. The catheter can be loaded with a suitable inhibitor or agent according to the invention. The catheter can be loaded by the operator or can come from the manufacturer preloaded with a suitable dosage. The design and requirements for catheters for intrathecal administration are known in the art.

Suitable agents according to the invention are inhibitors of cyclic guanosine monophosphate (cGMP)-dependent protein kinase Iα (PKGIα). The inhibitor preferentially inhibits isoenzyme I relative to isoenzyme II and inhibits isoform α relative to isoform β. The ratio of inhibition desirable is as high as possible, but suitable ratios include at least 2:1, at least 5:1, at least 10:1, and at least 20:1. The inhibitor preferably does not inhibit cAMP-dependent protein kinase or cGMP-dependent phosphodiesterases. A preferred compound according to the invention is Rp-8-[(4-Chlorophenyl)thio]-cGMPS triethylamine (Rp-8-CPT-cGMPS).

Pharmaceutical formulations can be made for treating pain in humans comprising Rp-8-CPT-cGMPS in a sterile, pyrogen-free aqueous vehicle. Any such pharmaceutically acceptable vehicle can be used, so long as it is suitable for the mode of administration to be used. For example, for injections, the vehicle must be pyrogen-free.

In some situations, the patient is also being treated with an anesthetic. The coadministration of an inhibitor of the present invention has the desirable effect of reducing the patient's threshold for the anesthetic. Thus less anesthetic can be used to achieve similar results using the specific inhibitors of the present invention. Co-administration may be separated in time, so long as the effect of the inhibitor is to lower the anesthetic threshold in the individual receiving both agents. Thus the inhibitor may be delivered before, after, or simultaneously with the the anesthetic, although administrations within about 24 hours are desirable. Suitable anesthetics include those standardly administered by inhalation as well as narcotic based anesthetics.

Pain patients can also be treated with other compounds which inhibit other enzymes in the pathway elucidated. Such inhibitors include any that inhibit NMDA receptors, neuronal nitric oxide synthase, or guanylyl cyclase. Numerous inhibitors of these proteins are known in the art and any can be used to more potently close down the pathway shown here to be involved in nociception.

Dosages can be readily determined by those of skill in the art and will depend on the particular route of administration. In rats, amounts between 1 and 100 μg were delivered intrathecally. For humans corresponding amounts will typically be in the range of 50 μg and 100 mg, depending on size of the human.

The biochemical pathway which has been demonstrated as involved in nociception is also implicated in inflammation, neuronal injury, and post-ischaemic injury. Thus the inhibitors of the present invention can also be administered to patients experiencing such disease conditions. Treatment of such inhibitors will ameliorate disease conditions and reduce symptom severity.

The findings of the present inventors lead to a number of preferred methods for identifying additional compounds which can be used similarly to Rp-8-CPTc-GMPS for treating pain and reducing the threshold for anesthetics. In one such method a compound is tested for the ability to inhibit PKG Iα and PKG Iβ. A compound is identified as a candidate drug useful in the treatment of pain if it selectively inhibits PKG Iα relative to PKG Iβ. Suitable selectivity ratios are at least 2, at least 5, at least 10, and at least 20. Selectivity is beneficial to reduce the possibility of unwanted side effects. Compounds can also be tested for the ability to inhibit PKG II. A compound which does not inhibit PKG II or inhibits PKG II less strongly than PKG Iα is desirable.

Another way to screen for additional selective inhibitors of PKG Iα employs whole cells. The cells can be contacted with a test compound. Transcription of PKG Iα gene or translation of PKG Iα or acitivity of PKG Iα in the cells is monitored. Any method known in the art for detecting a specific mRNA or protein can be used. These include without limitation, Northern blots, RT-PCR, western blots, immunoprecipitation, in situ hybridization, ELISA assay, enzyme assays, etc. A compound is identified as a candidate drug if it inhibits transcription, activity, or translation of PKG Iα. Specific inhibition is desirable. Thus it is desired that compounds identified not be general inhibitors of transcription, enzyme activity, or translation, but that they be specific for the gene/enzyme target. Specificity can be monitored and determined using control genes/proteins. The most stringent test for specificity is comparing the activity of the test compounds to related isoenzymes and isoforms, such as PKG II, PKG II, as well as related enzymes such as cAMP-dependent protein kinase and cGMP-dependent phosphodiesterase.

The following examples are provided by way of illustration and to provide experimental and manipulative details. They are not intended to define or limit the invention, which are defined by the claims.

EXAMPLES

Example 1

MATERIALS AND METHODS 1.1 Animals.

Male Sprague-Dawley rats (250–300 g) were housed in different cages on a standard 12 h/12 h light-dark cycle, with water and food pellets available ad libitum. The experiments were carried out with the approval of the Animal Care Committee at the University of Virginia and were consistent with the ethical guidelines of the National Institutes of Health and the International Association for the Study of Pain.

1.2 Immunohistochemistry.

For PKGIα and Iβ immunohistochemistry, fifteen animals were deeply anesthetized with pentobarbital sodium (60 mg/kg i.p.) and perfused with 4% paraformaldehyde in phosphate buffer (0.1 M, pH 7.4) at 0 h and 96 h after injection of saline (100 μl, 0.9%) or formalin (100 μl, 4%) into a hind paw. The whole spinal cord was removed, postfixed in the same fixative solution for 4 h, cryoprotected by immersing in 30% sucrose overnight at 4° C. and frozen-sectioned at 30 μm. Sections were processed for immunohistochemistry with the use of the conventional avidin-biotin-complex method (26). In brief, sections were incubated in polyclonal rabbit anti-PKGIα antibody (1:800; StressGen Biotechnologies Corp, Victoria, Canada) or in polyclonal rabbit anti-PKGIβ antibody (1:800; StressGen Biotechnologies Corp, Victoria, Canada) diluted in 0.01M phosphate-buffered saline (pH 7.4) containing 3% normal goat serum and 0.25% Triton X-100 for 48 h at 4° C., and then in biotinylated goat anti-rabbit IgG (1:200, Vector Lab) for 1 h at 37° C. and in avidin-biotin-peroxidase complex (1:100; Vector Lab) for 1 h at 37° C. The immune reaction product was visualized by catalysis of 3,3-diaminobenzidine by horseradish peroxidase in the presence of 0.01% $H_2O_2$.

For Fos immunohistochemistry, rats were perfused one hour after the behavioral test was done as described below. The lumbar spinal cord was removed and cut into 30 μm transverse sections. Sections were processed following the above-mentioned procedures except that the primary antibody was substituted with polyclonal rabbit anti-Fos antibody (1:4,000, Santa Cruz Biotechnology, Inc., CA).

Specificity controls for all antisera included the immunoadsorption of the primary antisera with excess of relevant antigens, the substitution of normal sera for the primary antisera and the omission of the primary antisera. All of these controls were negative revealing no sign of an immunohistochemical reaction.

1.3 Behavioral Testing.

The rats were implanted with an intrathecal catheter under pentobarbital anesthesia. A polyethylene (PE-10) tube was inserted into the subarachnoid space at the rostral level of the spinal cord lumbar enlargement through an incision at the atlanto-occipital membrane according to the method of Yaksh and Rudy (27). The animals were allowed to recover for 7 to 10 days before being used experimentally. Rats showing neurological deficits postoperatively were discarded.

The agent administered intrathecally was a selective, potent and cell-permeable inhibitor of PKGIα, Rp-8-[(4-Chlorophenyl)thio]-cGMPS triethylamine, (Rp-8-p-CPT-cGMPS) (RBI, MA) (28). The drug was dissolved in distilled water before administration. The animals were randomly assigned into four groups as follows: distilled water (control) (n=12); 10 μg of Rp-8-p-CPT-cGMPS (n=6); 20 μg of Rp-8-p-CPT-cGMPS (n=6); 30 μg of Rp-8-p-CPTcGMPS (n=6). The drug solution was injected intrathecally in a volume of 10 μl, followed by an injection of 10 μl of distilled water to flush the catheter. Fifteen minutes later, formalin (100 μl, 4%) was injected into a hind paw of the rat. In addition, four rats were alone treated intrathecally with Rp-8-p-CPT-cGMPS (30 μg) and another four rats were normal without any treatment.

Immediately following the formalin injection, each individual rat was placed in a transparent cage for observation of the formalin-injected paw. The pain-related behaviors, flinches and shakes, were assessed for the next 60 min by an experimenter who was unaware of the group assignment. The observational session was divided into two periods: a phasic period (0–10 min) and a tonic period (10–60 min). The mean number of flinches and shakes for each period of each treatment group was determined 1.4 Western Blot Analysis.

Thirty five rats were sacrificed by decapitation at 0 h (normal control), 24 h, 48 h and 96 h after injection of saline (100 μl) or formalin (100 μl, 4%) into a hind paw. Lumbar enlargement segments of the spinal cord were dissected, quickly frozen in liquid nitrogen and stored at −80° C. for later use. Frozen tissues were homogenized in the homogenization buffer (50 mM Tris-HCl, 0.1 mM EDTA, 0.1mM EGTA, 1 mM phenylmethylsulfonyl fluoride, 1 μM leupeptin, 2 μM pepstatin A, 0.1% 2-mercaptoethanol). The crude homogenate was centrifuged at 4° C. for 15 min at 3,000×g. The supernatants (100 μg) were heated for 5 min at 90° C. and then loaded onto 4% stacking/7.5% separating SDS-polyacrylamide gels. The proteins were electrophoretically transferred onto nitrocellulose membrane and blocked with 2% non-fat dry milk and subsequently incubated for 1 h with polyclonal rabbit anti-PKGIα antibody (1:500) and with monoclonal mouse anti-endothelium NOS (eNOS) antibody (1:500) (Transduction Labs). Normal lung was used as a positive control. Specific proteins were detected using horseradish peroxidase-conjugated anti-rabbit or anti-mouse secondary antibody and visualized using chemiluminescence reagents provided with the ECL kit (Amersham Life Sciences Inc, II) and exposure to film. The intensity of blots was quantified with densitometry (Personal Densitometer/IMAGEQUANT; Molecular Dynamics).

In some experiments, rats were injected intraperitoneally (i.p.) with an NMDA receptor antagonist, MK-801 (RBI, MA), a selective neuronal NOS inhibitor (nNOS), 7-Nitroindazole (7-NI, Alexis Biochemicals, CA) and a selective sGC inhibitor, 1H-[1,2,4]oxadiazolo[4,3-a]quinoxalin-1-one (ODQ, Alexis Biochemicals, CA), each day for 4 days (96 h). The doses of MK-801, 7-NI and ODQ used in the present study were determined regarding to the previous studies (29–31). The experiments were divided into five groups. Group 1 (n=4) as control: i.p. injection of saline (0.9%, 2 ml) or peanut oil (2 ml) 30 min prior to the subcutaneous injection of saline (0.9%, 100 μl). Groups 2 (n=4): i.p. injection of saline (0.9%, 2 ml) or peanut oil (2 ml) 30 min prior to the subcutaneous injection of formalin (4%, 100 μl). Groups 3, 4 and 5: i.p. injection of MK-801 (2 mg/kg in 2 ml saline, n=4), 7-NI (100 mg/kg in 2 ml peanut oil, n=4) and ODQ (100 mg/kg in 2 ml peanut oil, n=4), respectively, 30 min prior to the subcutaneous injection of formalin (4%, 100 μl). Lumbar enlargement segments were removed and western blot analysis was employed in the same manner as above.

1.5 Statistical Analysis.

The results from the immunohistochemistry, behavioral tests and western blot were statistically assessed by an analysis of variance. Intergroup differences were analyzed by the Newman-Keuls test. Data were assessed as mean±S.E.M. Significance was set at $p<0.05$.

RESULTS 1.6 Distribution of PKGIα and Iβ Immunoreactivity in the Spinal Cord

Immunohistochemical analysis revealed PKGIα immunoreactivity in the neuronal bodies and processes and in specific lamina in the spinal cord of the Inormal rats. The PKGIα immunoreactive ((PKGIα-IR) fibers were concentrated in the superficial laminae of the spinal cord. The PKGIα-IR fibers of varying density were noted in all segments of the spinal cord. Usually, the highest density of PKGIα-IR fibers occurred in the cervical and thoracic segments (FIG. 1A and 1B), the moderate density in the lumbar segments (FIG. 1C) and the lowest density in the sacral segments (FIG. 1D). A few isolated PKGIα-IR fibers were noted in the deep laminae of the dorsal horn, particularly in the cervical and thoracic segments.

Similar to the distribution of PKGIα-IR fibers, PKGIα-IR neurons also were seen in all segments of the spinal cord. These PKGIα-IR neurons were small (<20 μm) and appeared either oval, fusiform or round with few neuronal processes. Since the density of PKGIα-IR fibers was relatively lower at the sacral level, many PKGIα-IR perikarya were observed clearly in the sacral segments (FIG. 1d, arrows). At the other segment levels, higher density of PKGIα-IR fibers made most PKGIα-IR perikarya difficult to be observed. Only some PKGIα-IR perikarya were seen in the superficial laminae under high magnification (FIGS. 1a and 1c, arrows). A few weakly stained PKGIα-IR cells were noted in the ependymal cell layer around the central canal, in the intermediolateral nucleus and in the lateral spinal nucleus. No PKGIα-IR neurons were found in the deep laminae of the dorsal horn, the ventral horn or the white matter.

PKGIβ immunoreactivity was not detected or very weakly detected in all laminae of the spinal cord.

1.7 Effect of Rp-8-p-CPT-cGMPS on Formalin-induced Pain Behavior

Figure 2:
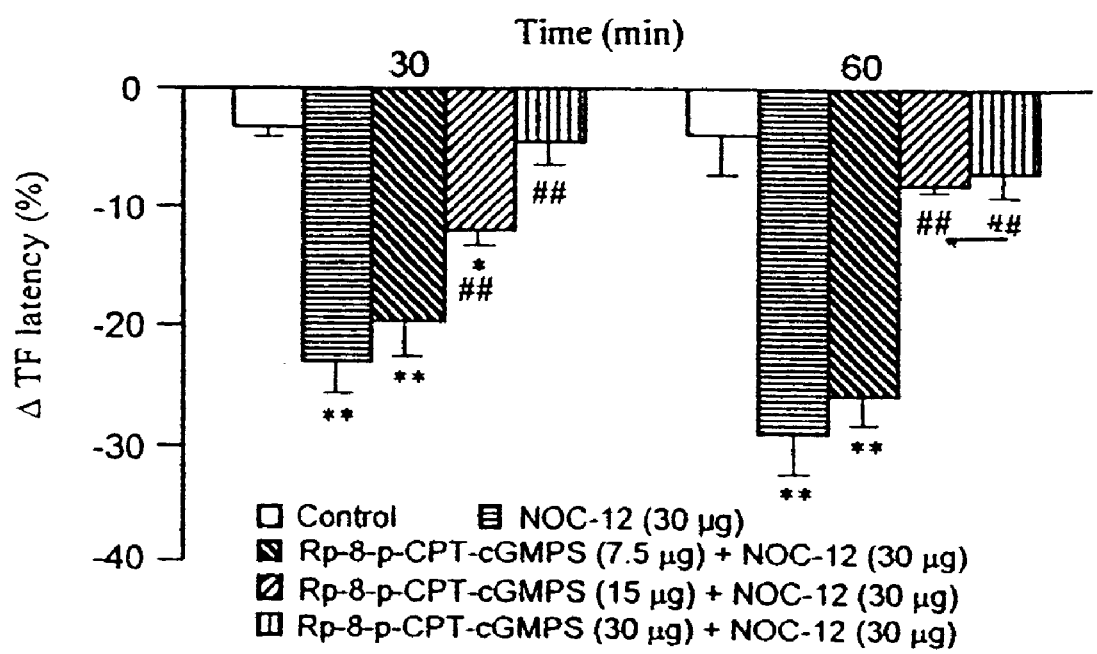
FIG. 2. Effect of intrathecally administered Rp-8-p-CPT-cGMPS on NOC-12-induced facilitation of the tail-flick latency when tested 30 and 60 min after the intrathecal administration of NOC-12. Data represent the mean±S.E.M. **$p<0.01$ or *$p<0.05$ vs saline control groups. ##$p<0.01$ vs NOC-12-treated groups.

Pretreatment with a selective PKGIα inhibitor, Rp-8-p-CPT-cGMPS, produced significant and dose-dependent decreases of formalin-induced pain behavior (FIG. 2). Intrathecal Rp-8-p-CPT-cGMPS at 30 μg reduced the number of flinches and shakes evoked by formalin by 64% ($p<0.01$) and 66% ($p<0.01$) in the phasic and tonic periods of the formalin test, respectively. Rp-8-p-CPTc-GMPS given at 20 μg dramatically suppressed the formalin-induced behavior by 25% ($p<0.01$) in the tonic period, but had no effect in the phasic period. 10 μg dose of Rp-8-p-CPT-cGMPS did not influence the formalin response in either the phasic or the tonic periods of the formalin test.

1.8 Effect of Rp-8-p-CPT-cGMPS on Formalin-Induced c-fos Expression in the Spinal Cord Numerous Fos-positive neurons were observed in the ipsilateral side of the spinal cord, while fewer Fos-positive neurons were detected in the contralateral side following the injection of formalin into a hind paw. Many Fos-positive neurons were distributed in the medial region of the superficial laminae and laminae V and VI, a few in laminae III, IV and X, and fewer in laminae VII–X (FIG. 3A). There were no Fos-positive neurons in the rats without any treatment or only with the treatment of Rp-8-p-CPT-cGMPS.

Figure 3:
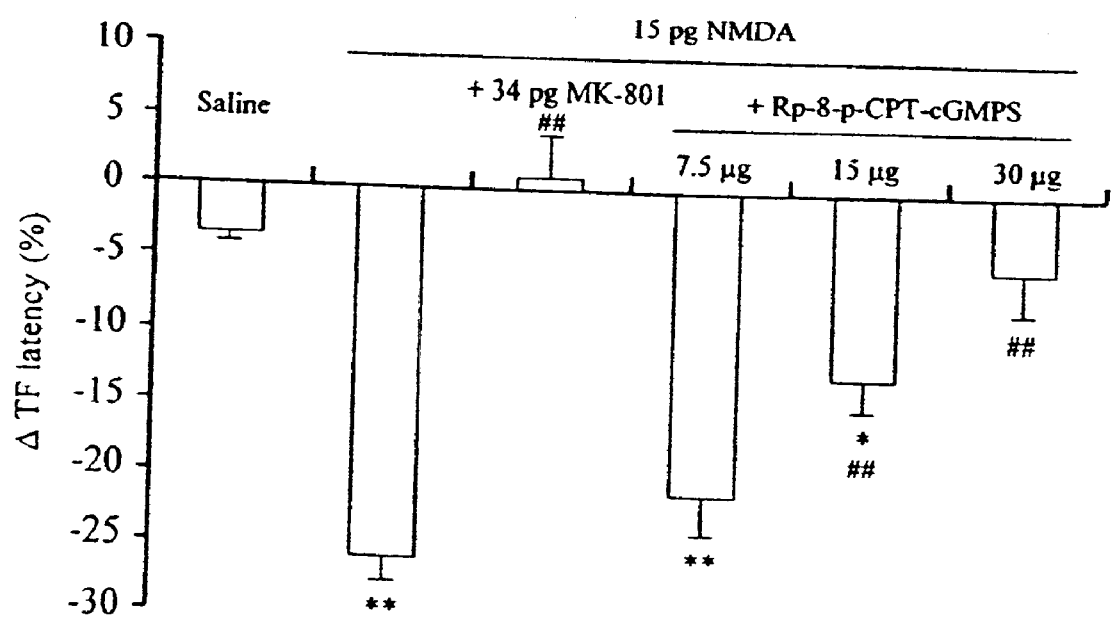
FIG. 3. Effects of MK-801 and Rp-8-p-CPT-cGMPS on NMDA-induced facilitation of the tail-flick latency when tested 30 min after the intrathecal administration of 10 pg NMDA. Data represent the mean±S.E.M. **$p<0.01$ or *$p<0.05$ vs saline-treated groups. ##$p<0.01$ vs NMDA-treated groups.
Figure 4:
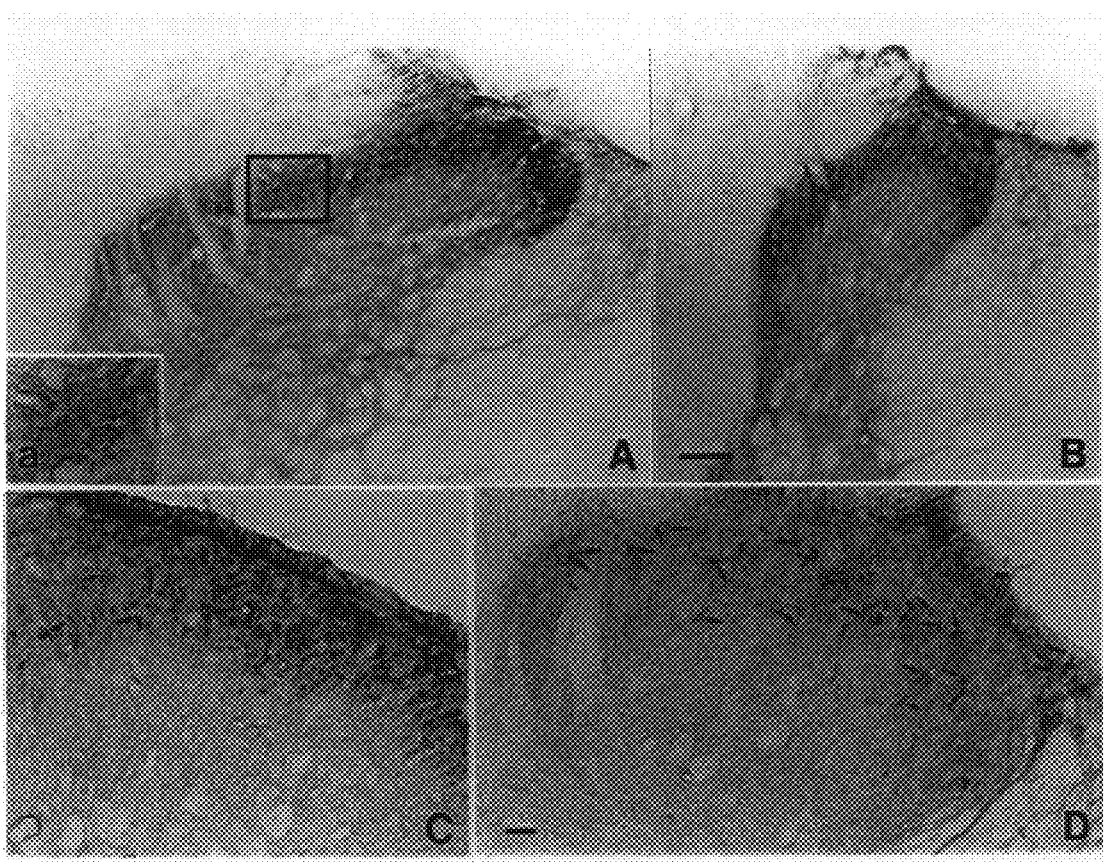
FIGS. 4(A–D). Photomicrographs showing the distribution of PKGIα immunoreactivity in the dorsal horn at different spinal segments. Cervical (A), thoracic (B), lumbar (C) and sacral (D) segments. PKGIα immunoreactivity was located mainly in the superficial laminae. a, c and d were high magnification of A, C and D, respectively, showing PKGIα-IR neuronal bodies (arrows). Scale bar: 200 μm.

Administration of Rp-8-p-CPT-cGMPS also significantly and dose-dependently attenuated formalin-induced c-fos expression in all laminae except for the ventral horn and the lamina X in the spinal cord (FIGS. 3B and 4). With a large dose of Rp-8-p-CPT-cGMPS (30 μg), the mean reduction in number of fos-positive neurons per section was 29% in the superficial laminae, and 30% in the nucleus proprius and 51% in the neck of dorsal horn as compared to the control group. The depression was statistically significant in the three regions ($p<0.05$). However, a low dose of Rp-8-p-CPT-cGMPS (10 μg) failed to produce any significant change of the amount or distribution of Fos-positive neurons as compared to the control group.

1.9 Upregulation of PKGIα Expression in the Spinal Cord after Formalin Injection Abundant PKGIα protein was detected only in the tissues from 96 h formalin-treated rats, while low levels were detected in tissues from the normal control rats, 24 h and 48 h formalin-treated rats and 24 h, 48 h and 96 h saline-treated rats (FIG. 5). Quantitation showed that the PKGIα protein levels were respectively 1.70- and 1.55-fold greater in tissues from the 96 h formalin-treated group (n=5) than those in tissues from the normal control (n=5) and the 96 h saline-treated (n=5) groups. The statistical analysis showed a significant difference ($p<0.05$) (FIG. 5). Tissues from the 24 h (n=5) and 48 h (n=5) formalin-treated groups contained 1.25- and 1.07-fold more PKGIα protein than those from the 24 h (n=5) and 48 h (n=5) saline-treated groups, but the increases were not statistically significant ($p>0.05$) (FIG. 5). The PKGIα protein levels also did not differ significantly in tissues from 24 h and 48 h formalin- or saline-treated animals and the normal control animals ($p>0.05$) (FIG. 5).

Figure 6:
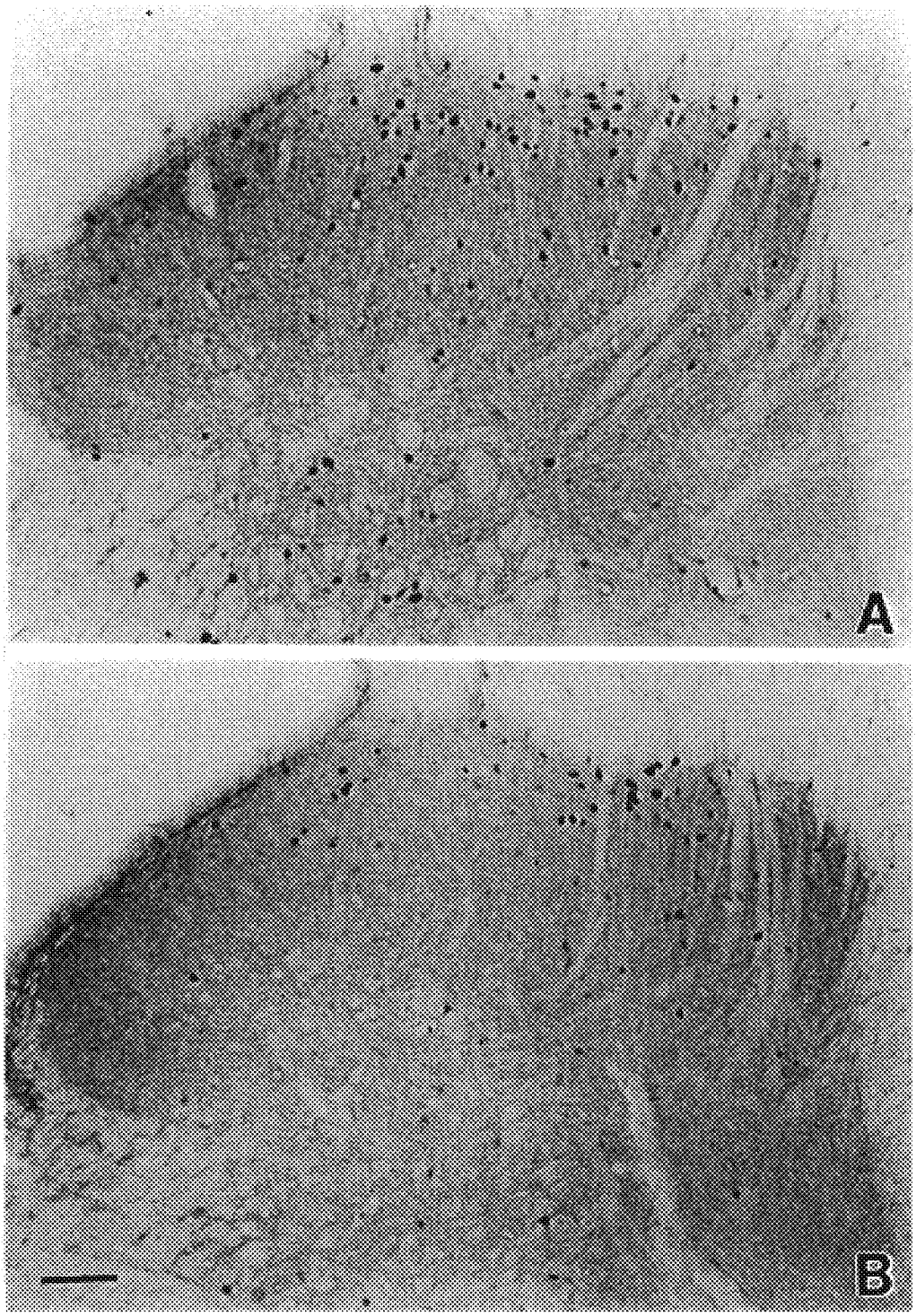
FIGS. 6(A–B) Photomicrographs showing the distribution of Fos-positive neurons in the dorsal horn of the fifth lumbar segment.
Figure 8A:
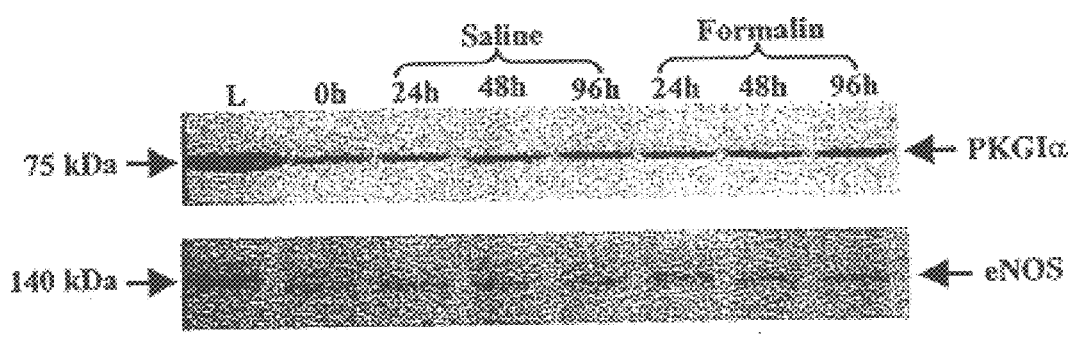
Figure 9:
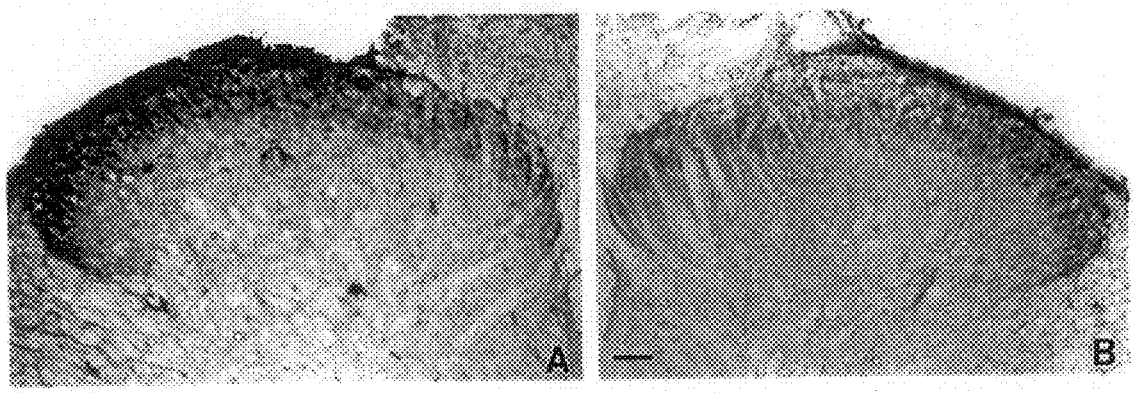
(FIG. 9A) the ipsilateral side.
(FIG. 9B) the contralateral side. There was a significant increase in optical density of PKGIα immunoreactivity throughout the superficial laminae on the formalin-treated side (FIG. 9A) but not on the normal side. Saline-treated animals did not show any changes in the optical density of PKGIα immunoreactivity on either side of the lumbar spinal cord. Scale bar: 200 μm.
Figure 10:
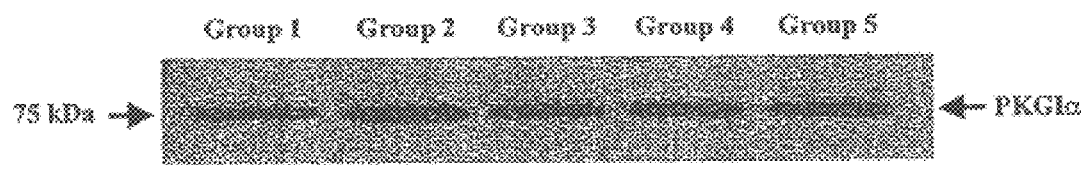
FIG. 10. Effects of intraperitoneally administered MK-801, 7-NI and ODQ on the PKGIα expression in the lumbar enlargement segments of the spinal cord from treated animals 96 hours after formalin injection. A representative western blot is shown. Lane I: group 1 (control); Lane II: group 2; Lane III: group 3; Lane IV: group 4; Lane V: group 5.

In the 96 h formalin-treated rats, the optical density of PKGIα immunoreactivity (fibers and cell bodies) increased throughout the superficial laminae in the lumbar segments. Particularly in the medial region of the superficial laminae, the dense PKGIα-IR fibers were observed (FIG. 6C) compared to those in the control or saline-treated groups. Under high magnification, some weakly staining PKGIα-IR perikarya were also found in the medial region of the superficial laminae. These changes occurred only on the ipsilateral side, not on the contralateral side (FIGS. 6C and D). The 96 h saline-treated animals did not show any changes in the optical density of PKGIα immunoreactivity on either side of the lumbar spinal cord (FIGS. 6A and B).

1.8 Effects of MK-801, 7-NI and ODQ on Formalin-induced Upregulation of PKGIα Expression in the Spinal Cord As shown in FIG. 7, after i.p. pretreatment with vehicle (saline or peanut oil), the tissues from 96 h formalin-treated rats (group 2) still displayed more abundant PKGIα protein in comparison with those from 96 h saline-treated rats (group 1). Quantitation showed that PKGIα protein level in group 2 was 1.52-fold greater than that in group 1. The statistical analysis showed significant difference between the two groups above ($p<0.05$). However, following i.p. pretreatment with MK-801, 7-NI or ODQ, the tissues from 96 h formalin-treated rats (groups 3, 4 and 5) did not show marked increase in PKGIα protein (FIG. 7). Quantitation revealed that the PKGI' protein levels in groups 3, 4 and 5 were respectively 1.13, 1.17 and 1.14-fold greater than that in group 1, but the increases were not statistically significant ($p>0.05$) (FIG. 7).

Example 2

The previous example showed that cGMP-dependent protein kinase Iα but not Iβ was distributed primarily in the superficial laminae of the spinal cord. The purpose of the present study was to determine whether the thermal hyperalgesia produced by NMDA or NO is mediated through the activation of cGMP-dependent protein kinase Iα.

Materials and methods 2.1. Subjects

Male Sprague-Dawley rats weighing 250–300 g were used. They were kept under a standard 12 h/12 h light-dark cycle, with water and food pellets available ad libitum. The experimental procedures were approved by the Animal Care Committee at the Johns Hopkins University and were consistent with the ethical guidelines of the National Institute of Health and the International Association for the Study of Pain.

The agents administered intrathecally in th e present study were RP-8-[(4-Chlorophenyl)thio]-cGMPS triethylamine (Rp-8-p-CPT-cGMPS, a selective and potent cGMP-dependent protein kinase Iα inhibitor) (RBI, MA, USA), N-ethyl-2-(1-ethyl-2-hydroxy-2-nitrosohydrazino) ethanamine (NOC-12, an NO donor) (Alexis Biochemicals, CA, USA), NMDA (an NMDA receptor agonist) (RBI, MA, USA) and dizocilpine maleate (MK-801, a selective NMDA receptor antagonist) (RBI, MA, USA).

2.2. Surgery

Rats were anesthetized by intraperitoneal injection of pentobarbital sodium (45 mg/kg). Chronic intrathecal catheters were inserted by passing a polyethylene-10 (PE-10) catheter through an incision in the atlanto-occipital membrane to a position 8 cm caudal to the cisterna at the level of the lumbar subarachinoid space. The animals were allowed to recover for a week before experiments were initiated. Rats showing neurologic deficits post-operatively were removed from the study.

2.3. Thermal Nociceptive Test

Nociception was evaluated by the radiant heat tail-flick test with no anesthesia. Each rat was placed in an Animal Holder (IITC Life Science, CA, USA), 690 cm$^3$ in capacity with rubber stoppers in both ends with a rostral inlet and a caudal outlet. The tail of the rat protruded through the caudal hole. The tail-flick apparatus (Model 33B Tail Flick Analgesy Meter, IITC Life Science, CA, USA) generated a beam of radiant heat which was focused on the underside of the tail, 5 cm from the tip. A cut-off time latency of 13.5 s was used to avoid tissue damage to the tail. Nociception was assessed by the prolongation of the time required to induce tail-flick after applying radiant heat to the skin of the tail. The latency of reflexive removal of the tail from the heat was measured automatically to the nearest 0.01 s. Tail-flick latency was measured six times and the basal latency was defined as the mean of the last five times. The tail-flick data are expressed as percentage change calculated by the formula: (trial latency—baseline latency)/(baseline latency)× 100%.

2.4. Drug Treatment

The rats were randomly assigned into fifteen groups as follows: saline (control) (n=6); 7.5 μg of Rp-8-p-CPT-cGMPS (n=6); 15 μg of Rp-8-p-CPT-cGMPS (n=6); 30 μg of Rp-8-p-CPT-cGMPS (n=6); 10 μg of NOC-12 (n=6); 20 μg of NOC-12 (n=6); 30 μg of NOC-12 (n=6); 7.5 μg of Rp-8-p-CPT-cGMPS and 30 μg of NOC-12 (n=6); 15 μg of Rp-8-p-CPT-cGMPS and 30 μg of NOC-12 (n=6); 30 μg of Rp-8-p-CPT-cGMPS and 30 μg of NOC-12 (n=6); 15 pg of NMDA (n=5); 34 pg of MK-801 and 15 μg of NMDA (n=5); 7.5 pg of Rp-8-p-CPT-cGMPS and 15 pg of NMDA (n=5); 15 μg of Rp-8-p-CPT-cGMPS and 15 μg of NMDA (n=5); 30 μg of Rp-8-p-CPT-cGMPS and 15 pg of NMDA (n=5). The dose and time point of maximal effect of NMDA used above was Idetermined based on a previous study (Siegan and Sagen, 1995). The drug solution was injected intrathecally in a volume of 10 μl, followed by an injection of 10 μl of saline to flush the catheter. The tail-flick test was conducted before injection and 15, 30, 60, 90 and 120 min after injection.

2.5. Data Analysis

Data were expressed as the mean±S.E.M. The results were assessed by an analysis of variance followed by Newman-Keuls test. Significance was set up at p<.

Results

No significant change in the tail-flick latency was seen before and after the injection of saline (FIG. 1, p>0.05). The intrathecal administration of NOC-12 produced a dose-dependent decrease of the tail-flick latency during the period from 15 to 90 min with a maximum effect at 60 min (The baseline tail flick latency was maximally reduced from 6.53±0.28 to 4.65±0.32 seconds with the use of 30 μg NOC-12. FIG. 1, p<0.01). The maximal decreases in the tail-flick latency (%) after administration of 10, 20 and 30 μg of NOC-12 were 5.4%, 18.5% (FIG. 1, p<0.01) and 24.9% (FIG. 1, p<0.01), respectively, compared to control (saline-treated group). The hyperalgesia evoked by NOC-12 was no longer observed 120 min after intrathecal injection.

Three doses of Rp-8-p-CPT-cGMPS (7.5, 15 and 30 μg) given alone had no significant effect on the baseline tail-flick latency between 15 and 120 min. after administration (p>0.05). However, pretreatment (10 min prior) with two high doses of Rp-8-p-CPT-cGMPS (15 and 30 μg) significantly blocked the NOC-12-induced decrease in the tail-flick latency when tested 30 and 60 min after the administration of 30 μg of NOC-12 (FIG. 2, p<0.01), although a low dose of Rp-8-p-CPT-cGMPS (7.5 μg) did not influence the hyperalgesia induced by NOC-12 (FIG. 2, p>0.05).

Consistent with the previous results (Meller et al., 1992a, b; Siegan and Sagen, 1995), intrathecal administration of NMDA induced a significant facilitation of the tail-flick reflex (The baseline tail-flick latency was reduced from 6.58±0.57 to 4.88±0.41 seconds. FIG. 3, p<0.01). The NMDA-produced facilitation of the tail-flick reflex was not only completely abolished by prior treatment with NMDA receptor antagonist, MK-801 (FIG. 3, p<0.01), but also dose-dependently blocked by prior administration with Rp-8-p-CPT-cGMPS. Rp-8-p-CPT-cGMPS given at 15 and 30 μg dramatically suppressed the NMDA-induced decrease of the tail-flick latency by 13.3% (FIG. 3, p<0.01) and 20.7% (FIG. 3, p<0.01), respectively. Rp-8-p-CPT-cGMPS at 7.5 μg failed to produce significant effect on the NMDA-evoked facilitation of the tail-flick reflex (FIG. 3, p>0.05).

Subjective observation of rats injected with Rp-8-p-CPT-cGMPS, NOC-12, Rp-8-p-CPT-cGMPS+NOC-12, Rp-8-p-CPT-cGMPS+NMDA and MK-801+NMDA revealed no obvious changes in animal behavior during a period of 2 h when compared with control animals, Although intrathecal administration of NMDA to some rats produced a caudally directed biting and scratching behaviors. No sedative or toxic effect was observed after intrathecal administration of any of the agents used in this study.

Animal models used in these studies correlate well with humans, including nociception and anesthetic thresholds.

References

1. Bredt, D. S., Hwang, P. M., and Snyder, S. H. (1990) *Nature* 347, 768–670
2. Snyder, S. H. (1992) *Science* 257, 494–496
3. Garthwaite, J., Charles, S. L., and Chess-Williams, R. (1988) *Nature* 336, 385–388
4. Meller, S. T., and Gebhart, G. F. (1993) *Pain* 52, 127–136
5. Kitto, K. F., Haley, J. E., and Wilcox, G. L. (1992) *Neurosci. Lett.* 148, 1–5
6. Herdegen, T., Rudiger, S., Mayer, B., Bravo, R., and Zimmermann, M. (1994) *Mol. Brain Res.* 22, 245–258
7. Lam, H. H., Hanley, D. F., Trapp, B. D., Saito, S., Raja, S., Dawson, T. M., and Yamaguchi, H. (1996) *Neurosci. Lett.* 210, 201–204
8. Wu. J., Lin, Q., Lu, Y., Willis, W. D., and Westlund, K. N.(1998) *Exp. Brain Res.* 118, 457–465
9. Garry, M. G., Richardson, J. D., and Hargreaves, K. M. (1994) *Brain Res.* 646, 135–139
10. Moore, P. K., Oluyomi, A. O., Babbedge, R. C., Wallace, P., and Hart, S. L. (1990) *Br. J. Pharmacal.* 102, 198–202
11. Haley, J. E., Sullivan, A. F., and Dickenson, A. H. (1990). *Brain Res.* 518, 218–226
12. Meller, S. T., Dykstra, C., and Gebhart, G. F. (1992) *Eur. J. Pharmacol.* 214, 93–96
13. Malmberg, A. B., and Yaksh, T.L. (1993) *Pain* 54, 291–300
14. Machelska, H., Labuz, D., Przewlocki, R., Przewlocka, B. (1997) *J. Pharmacol. Exp. Ther.* 282, 977–984
15. Xu, J. Y., and Tseng, L. F. (1995) *J. Pharmacol. Exp. Ther.* 274, 8–16
16. Xu, J. Y., Hill, K. P., and Bidlack, J. M. (1998) *J. Pharmacol. Exp. Ther.* 284, 196–201

17. Garry, M. G., Abraham, E., Hargreaves, K. M., and Aanonsen, L. M. (1994) *Eur. J. Pharmacol.* 260, 129–131
18. Niedbala, B., Sanchez, A., and Feria, M. (1995) *Neurosci. Lett.* 188, 57–60
19. Inoue, T., Mashimo, T., Shibata, M., Shibuta, S., and Yoshiya, I. (1998) *Brain Res.* 792, 263–270
20. Inoue, T., Mashimo, T., Shibuta, S., and Yoshiya, I. (1997) *J.Neurological. Sci.* 153, 1–7
21. Garry, M. G., Richardson, J. D., and Hargreaves, K. M. (1994) *J. Neurosci.* 14, 4329–4337
22. Knowles, R. G., Palacios, M., Palmar, R. M. J., and Moncada, S. (1989) *Proc. Natl. Acad. Sci. USA.* 86, 5159–5162
23. Moncada, S., Palmar, R. M. J., and Higgs, E. A. (1991) *Pharmacol. Rev.* 43, 109–142
24. Lincoln, T. M., and Cornwell, T. L. (1993) *FASEB* 7, 328–338
25. Lincoln, T. M., Komalavilas, P., and Cornwell, T. L. (1994) *Hypertension* 23, 1141–1147
26. Hsu, S.-M., Raine, L., and Fanger, H. A. (1980) *J. Histochem. Cytochem.* 29, 577–580
27. Yaksh, T. L., and Rudy, T. A. (1976) *Science* 192, 1357–1358
28. Butt, E., Eigenthaler, M., and Genieser H.-G. (1994) *Eur. J. Pharmacol.* 269,265–268
29. Iwasaki, Y., Ikeda, K., Shiojima, T., and Kinoshita, M. (1995) *J. Neurological. Sci.* 134, 21–25
30. Ji, R. R., and Rupp, F. (1997) *J. Neurosci.* 17, 1776–1785
31. Pajewski, T. N., Difazio, C. A., Moscicki, J. C., and Johns, R. A. (1996) *Anesthesiology* 85, 1111–1119
32. Wang, X., and Robinson, P. J. (1997) *J. Neurochem.* 68,443–456
33. Lincoln, T. M., Klockhart, D. A., and Corbin, J. D. (1978) *J. Biol. Chem.* 253, 6002–6009
34. Qian, Y., Chao, D. S., Santillano, D. R., Cornwell, T. L., Naim, A. C., Greengard, P., Lincoln, T. M., and Bredt, D. S. (1996) *J. Neurosci.* 16, 3130–3138
35. Rustioni, A., and Weinberg, R. J. (1989) The somatosensory system. In: Handbook of Chemical Neuroanatomy (Bjorklund A, Hokfelt T, Swanson L W, eds), pp219–321. Amsterdam: Elsevier.
36. Lin, Q., Peng, Y. B., Wu, J., and Willis, W. D. (1997) *J. Neurosci.* 17, 3293–3302
37. Sluka, K. A., and Willis, W. D. (1997) *Pain* 71, 165–178
38. TjΦ sen, A., Berge, O.-G., Hunskaar, S., Rosland, J. H., and Hole, K. (1992) *Pain* 51, 5–17
39. Bullitt, E. (1990) *J. Comp. Neurol.* 296, 517–530
40. Tao, Y.-X., and Zhao, Z.-Q. (1997) *Neuropeptides* 31, 327–332
41. Mccarson, K. E., and Goldstein, B. D. (1989) *Pain* 38, 339–345
42. Goff, J. R., Burkey, A. R., Goff, D. J., and Jasmin, L. (1998) *Neuroscience* 82, 559–574
43. Paxinos, A. (1990) *The human nervous system*, Academic Press, New York, pp819
44. Dawson, T. M., and Synder, S. H. (1994) *J. Neurosci.* 14, 5202–5222
45. Mao, J., Price, D. D., Coghill, R. C., Mayer, D. J., and Hayes, R. L. (1992) *Pain* 50, 89–100
46. Zhou, M., Hu, Y., Schultz, C., Kandel, E. R., and Hawkins, R. D. (1994) *Nature* 368, 635–639
47. Valtschanoff, J. G., Weinberg, R. J., Rustioni, A., Schmidt, H. H. H. W. (1992) *Neurosci. Lett.* 148, 6–10
48. Dun, N. J., Dun, S. L., Wu, S. Y., Forstermann, U., Schmidt, H. H., and Tseng, L. F. (1993) *Neuroscience* 54, 845–857
49. Aanonsen, L. M., Lei, S., Wilcox, G. L., 1990. Excitatory amino acid receptors and nociceptive neurotransmission in the rat spinal cord. Pain 41, 309–321.
50. Bredt, D. S., Snyde, S. H., 1992. Nitric oxide, a novel neuronal messenger. Neuron 8, 3–11.
51. Butt, E., Eigenthaler, M., Genieser, H.-G., 1994. (Rp)-8-pCPT-cGMPS, a novel cGMP-dependent protein kinase inhibitor. Eur. J. Pharmacol. 269, 265–268.
52. Dickenson, A. H., Aydar, E., 1991. Antagonism at the glycine site on the NMDA receptor reduces spinal nociception in the rat. Neurosci. Lett. 121, 263–266.
53. Garthwaite, J., Charles, S. L., Chess-Williams, R., 1988. Endothelium-derived relaxing factor release on activation of NMDA receptors suggests role as intracellular messenger in the brain. Nature 336, 385–388.
54. Garry, M. G., Abraham, E., Hargreaves, K. M., Aanonsen, L. M., 1994a. Intrathecal injection of cell-permeable analogs of cyclic 3', 5'-guanosine monophosphate produces hyperalgesia in mice. Eur. J. Pharmacol. 260, 129–131.
55. Garry, M. G., Richardson, J. D., Hargreaves, K. M., 1994b. Carrageenan-induced inflammation alters the content of i-cGMP and i-cAMP in the dorsal horn of the spinal cord. Brain Res. 646, 135–139.
56. Garry, M. G., Richardson, J. D., Hargreaves, K. M., 1994c. Sodium nitroprusside evokes the release of immunoreactive calcitonin gene-related peptide and substance P from dorsal horn slices via nitric oxide-dependent and nitric oxide-independent mechanisms. J. Neurosci. 14, 4329–4337.
57. Inoue, T., Mashimo, T., Shibuta, S., Yoshiya, I., 1997. Intrathecal administration of a new nitric oxide donor, NOC-18, produces acute thermal hyperalgesia in the rat. J. Neurological. Sci. 153, 1–7.
58. Kiedrowski, L., Costa, E., Wroblewski, J. T., 1992. Glutamate receptor agonists stimulate nitric oxide synthase in primary cultures of cerebellar granule cells. J. Neurochem. 58, 335–41.
59. Lam, H. H., Hanley, D. F., Trapp, B. D., Saito, S., Raja, S., Dawson, T. M., Yamaguchi, H., 1996. Induction of spinal cord neuronal nitric oxide synthase (NOS) after formalin injection in the rat hind paw. Neurosci. Lett. 210, 201–204.
60. Lincoln, T. M., Cornwell, T. L., 1993Intracellular cyclic GMP receptor proteins. FASEB 7, 328–338.
61. Malmberg, A. B., Yaksh, T. L., 1993. Spinal nitric oxide synthesis inhibition blocks NMDA-induced thermal hyperalgesia and produced antinociception in the formalin test in rats. Pain 54, 291–300.
62. Meller, S. T., Dykstra, C., Gebhart, G. F., 1992a. Production of endogenous nitric oxide and activation of soluble guanylate cyclase are required for N-methyl-D-aspartate-produced facilitation of the nociceptive tail-flick reflex. Eur. J. Pharmacol. 214, 93–96.
63. Meller, S. T., Gebhart, G. F., 1993. Nitric oxide (NO) and nociceptive processing in the spinal cord. Pain 52, 127–136.
64. Meller, S. T., Pechman, P. S., Gebhart, G. F., Maves, T. J., 1992b. Nitric oxide mediates the thermal hyperalgesia produced in a model of neuropathic pain in the rat. Neuroscience 50, 7–10.
65. Moore, P. K., Oluyomi, A. O., Babbedge, R. C., Wallace, P., Hart, S. L., 1990. L-$N^G$-nitro arginine methyl ester exhibits antinociceptive activity in the mouse. Br. J. Pharmacol. 102, 198–202.
66. Rivot, J.-P., Sousa, A., Montagne-Clavel, J., Besson, J.-M., 1999. Nitric oxide (NO) release by glutamate and NMDA in the dorsal horn of the spinal cord: an in vivo electrochemical approach in the rat. Brain Res. 821, 101–110.

67. Rustioni, A., Weinberg, R. J., 1989. The somatosensory system. In: Handbook of Chemical Neuroanatomy (Bjorklund A, Hokfelt T, Swanson L W, eds), pp219–321. Amsterdam: Elsevier.
68. Siegan, J. B., Sagen, J., 1995. Attenuation of NMDA-induced spinal hypersensitivity by adrenal medullary transplants. Brain Res. 680, 88–98.
69. Sluka, K. A., Willis, W. D., 1997. The effects of G-protein and protein kinase inhibitors on the behavioral responses of rats to intraderinal injection of capsaicin. Pain 71, 165–178.
70. Tao, Y.-X., Hassan, A., Haddad, E., Johns, R. A., 2000. Expression and action of cyclic GMP-dependent protein kinase Iα in inflammatory hyperalgesia in rat spinal cord. Neuroscience 95,525–533.

What is claimed is:

1. A method of affecting nociception, comprising:
   administering to a patient in need thereof an analgesic amount of an inhibitor of cyclic guanosine monophosphate (cGMP)-dependent protein kinase Iα (PKGIα) wherein said inhibitor preferentially inhibits isoenzyme II and inhibits isoform α relative to isoform β.
2. The method of claim 1 wherein the patient experiences chronic pain.
3. The method of claim 1 wherein the patient experiences acute pain.
4. The method of claim 1 wherein the patient experiences inflammatory hyperalgesia.
5. The method of claim 1 wherein the patient experiences spinal hyperalgesia.
6. The method of claim 1 wherein the patient is receiving anesthetic whereby upon administering said inhibitor the threshold for said anesthetic is reduced.
7. The method of claim 1 wherein the mode of administration is intrathecal.
8. The method of claim 1 wherein the inhibitor does not inhibit cAMP-dependent protein kinase or cGMP-dependent phosphodiesterases.
9. The method of claim 1 wherein the inhibitor is Rp-8-[(4-Chlorophenyl)thio]-cGMPS triethylamine (Rp-8-CPT-cGMPS).
10. A method of affecting nociception, comprising:
    administering intrathecally to a patient in need thereof an analgesic amount of Rp-8-[(4-Chlorophenyl)thio]-cGMPS triethylamine (Rp-8-CPT-cGMPS).
11. The method of claim 10 wherein the patient experiences acute pain.
12. The method of claim 10 wherein the patient experiences inflammatory hyperalgesia.
13. The method of claim 10 wherein the patient experiences spinal hyperalgesia.
14. The method of claim 10 wherein the patient is receiving anesthetic whereby upon administering said inhibitor the threshold for said anesthetic is reduced.
15. The method of claim 1 further comprising administering an NMDA receptor inhibitor to the patient.
16. The method of claim 15 wherein the NMDA receptor inhibitor is ketamine.
17. The method of claim 15 wherein the NMDA receptor inhibitor is MK-801.
18. The method of claim 1 further comprising administering an inhibitor of neuronal nitric oxide synthase (nNOS) to the patient.
19. The method of claim 18 wherein the inhibitor of nNOS is $N^G$-nitro-L-arginine methyl ester (L-NAME).
20. The method of claim 18 wherein the inhibitor of nNOS is 7-nitroindazole.
21. The method of claim 18 wherein the inhibitor of nNOS is 3'-bromo-7-nitro indazole.
22. The method of claim 1 further comprising administering an inhibitor of guanylyl cyclase.
23. The method of claim 22 wherein the inhibitor of guanylyl cyclase is ODQ.
24. The method of claim 22 wherein the inhibitior of guanylyl cyclase is methylene blue.

* * * * *

UNITED STATES PATENT AND TRADEMARK OFFICE
CERTIFICATE OF CORRECTION

PATENT NO. : 6,476,007 B2  Page 1 of 1
APPLICATION NO. : 09/731876
DATED : November 5, 2002
INVENTOR(S) : Yuanxiang Tao et al.

It is certified that error appears in the above-identified patent and that said Letters Patent is hereby corrected as shown below:

In Column 15, Claim 1, Line 21-22:
Please replace "inhibits isoenzyme II" with --inhibits isoenzyme I relative to isoenzyme II--

Signed and Sealed this

Second Day of January, 2007

JON W. DUDAS
*Director of the United States Patent and Trademark Office*